US005258377A

United States Patent [19]

Maiti et al.

[11] Patent Number: 5,258,377

[45] Date of Patent: Nov. 2, 1993

[54] 2-SPIROCYCLOPROPYL 4-ACYLCEPHEMS

[75] Inventors: Samarendra N. Maiti; Narender A. V. Reddy; David Czajkowski; Paul Spevak; Charles Fiakpui, all of Edmonton; Ronald G. Micetich, Sherwoodk Park, all of Canada

[73] Assignee: Taiho Pharmaceutical Co., Ltd., Tokyo, Japan

[21] Appl. No.: 681,680

[22] Filed: Apr. 8, 1991

[51] Int. Cl.[5] .................. C07D 501/57; A61K 31/545

[52] U.S. Cl. .................................... 514/201; 514/202; 514/206; 540/221; 540/222; 540/225; 540/226; 540/227

[58] Field of Search ............... 540/222, 227, 226, 221, 540/225, 230; 514/201, 202, 203, 206

[56] References Cited

U.S. PATENT DOCUMENTS

| | | | |
|---|---|---|---|
| 3,883,517 | 5/1975 | Heusler et al. | 260/243 C |
| 4,547,371 | 10/1985 | Doherty et al. | 514/200 |
| 4,717,722 | 1/1988 | Doherty et al. | 514/210 |
| 5,077,286 | 12/1981 | Bissolino et al. | 540/221 |

FOREIGN PATENT DOCUMENTS

| | | |
|---|---|---|
| 80624/87 | 5/1988 | Australia . |
| 32762/89 | 10/1989 | Australia . |
| 124081 | 11/1984 | European Pat. Off. . |
| 0267723 | 5/1988 | European Pat. Off. . |
| 0337704 | 10/1989 | European Pat. Off. . |
| 1-226887 | 9/1989 | Japan . |
| WO89/10926 | 11/1989 | PCT Int'l Appl. . |

OTHER PUBLICATIONS

Hagmann et al., *Eur. J. Med. Chem.*, 24, pp. 599–604 (1989).

Blacklock et al., *J. Org. Chem.*, 54, pp. 3907–3913 (1989).

Wright et al., *J. Med. Chem.*, vol. 14, pp. 420–429 (1971).

Fletcher et al., *Am. Rev. Respir. Dis.*, 141, pp. 672–677 (1990).

Gunda, *Liebigs Ann. Chem.*, pp. 311–312 (1990).

Kaiser et al., *J. Med. Chem.*, 14, 426–429 (1971).

Jaszberenyi et al., *Mag. Res. Chem.*, vol. 26, pp. 658–664 (1988).

Bonney et al., *J. Cell. Biochem.*, 39, pp. 47–53 (1989).

*Annual Reports in Medicinal Chemistry*, 24, Chap. 7, p. 68, edited by R. C. Allen, Academic Press, Inc. (1989).

Navia et al., *Nature*, vol. 327, pp. 79–82 (1987).

*Annual Drug Data Report*, 7(4), 263 (1985).

*Annual Drug Data Report*, 10(11), 868 (1988).

*Annual Drug Data Report*, 11(6), 459 (1989).

*Annual Drug Data Report*, 12(10), 785 (1990).

*J. Med. Chem.*, 33, 2513–2521 (1990).

*J. Med. Chem.*, 33, 2522–2528 (1990).

*J. Med. Chem.*, 33, 2529–2535 (1990).

*J. Liquid Chromatography*, 12(15), 2961–2969 (1989).

*Annual Drug Data Report*, 13(1), 24 (1991).

*Annual Drug Data Report*, 12(2), 116 (1990).

*Annual Drug Data Report*, 12(6), 458 (1990).

Alpegiani et al., Bioorganic & Medical Chemistry Letters, vol. 2, No. 9, pp. 1127–1132, 1992.

Doherty et al., "Cephalosporin antibiotics can be modified to inhibit human leukocyte elastase", *Nature*, 322, 192–194 (Jul. 10, 1986).

Pitlick et al., *J. Heterocyclic Chem.*, 26, 461–464 (1989).

*Primary Examiner*—Nicholas S. Rizzo

*Attorney, Agent, or Firm*—Nikaido, Marmelstein, Murray & Oram

[57] ABSTRACT

Derivatives of 2-spirocyclopropyl 4-acylcephem sulfones of the formula (I)

(I)

are provided which are useful as potent elastase inhibitors and hence are useful in the prevention, control and treatment of inflammatory conditions, especially arthritis and emphysema.

13 Claims, No Drawings

2-SPIROCYCLOPROPYL 4-ACYLCEPHEMS

BACKGROUND OF THE INVENTION

Serine proteases are an important class of enzymes which have a serine residue at the active site. Elastase is one such serine protease which is released from azurophilic granules of human polymorphonuclear leukocytes (PMN) and macrophages by inflammatory stimuli. Human leukocyte elastase (HLE) has been reported to be capable of degrading the connective tissue component elastin in addition to a number of other connective tissue substrates resulting in a variety of clinically important imflammatory diseases e.g. pulmonary emphysema, rheumatoid arthritis, spondylitis, psoriasis, osteoarthritis, chronic bronchitis, cystic fibrosis, and respiratory distress syndrome (RDS). Under normal conditions, the proteolytic activity of elastase in the extracellular environment is limited by the presence of excess of natural inhibitors like $\alpha_1$ protease inhibitor ($\alpha_1$ PI) and $\alpha_2$ macroglobulin. Marked reduction in serum $\alpha_1$PI either genetic or due to oxidants, results in protease-antiprotease imbalance and thus leads to uncontrolled proteolysis of connective tissue, primarily of the lung and joints [J. Travis et al. *Ann. Rev. Biochem.*, 52, 655 (1983)]. Pulmonary emphysema is a disease characterized by a progressive loss of lung elasticity and resulting in respiratory difficulty. This loss of lung elasticity is caused by progressive destruction of the structure of lung tissue by elastase released from leukocytes. Use of low molecular weight synthetic human leukocyte elastase (HLE) inhibitors would be an ideal therapeutic approach in controlling the various inflammatory conditions.

Cephem sulfones have been described as elastase inhibitors in various patents and publications. See, for example, U.S. Pat. No. 4, 547,371; EP patent nos. 267,723 and 337,704; AU patent nos. 80624/87 and 32762/89; *J. Med. Chem.*, 33, 2513 (1990); *J. Med. Chem.*, 33, 2522 (1990); *J. Med. Chem.*, 33, 2529 (1990); *J. Org. Chem.*, 54, 3907 (1989), *Eur. J. Med. Chem.*, 24, 599 (1989); *Am. Rev. Respir. Dis.*, 141, 672 (1990); *J. Cell. Biochem.*, 39, 47 (1989); and *Nature*, 322, 192 (1986).

BRIEF SUMMARY OF THE INVENTION

We have found that a group of new substituted cephalosporin sulfones are potent elastase inhibitors and hence are useful as anti-inflammatory or anti-degenerative agents. Accordingly, an object of this invention is to provide new elastase inhibitors which are useful for controlling various clinically important inflammatory or degenerative conditions mediated particularly by elastase.

Another object of the present invention is to provide a pharmaceutical or veterinary composition for administering the active substituted cephalosporin sulfones as elastase inhibitors. Another object of the present invention is to provide a method of controlling inflammatory and degenerative diseases by administering a therapeutically effective amount of one or more of the active compounds of the present invention represented by the formula (I) in humans or warm-blooded mammalians in need of such treatment.

The present invention relates to 2-spirocyclopropyl 4-acylcephem sulfones, their preparation, and to pharmaceutical and veterinary compositions containing them.

In one aspect, the present invention relates to a 2-spirocyclopropyl 4-acylcephem sulfone of the formula

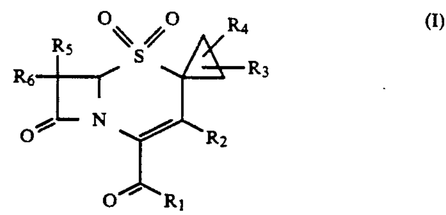

(I)

wherein $R_1$ is hydrogen; or $C_{1-12}$ straight or branched alkyl; or $C_{2-10}$ alkenyl; or $C_{2-10}$ alkynyl; or $C_{3-8}$ cycloalkyl; or $C_{5-8}$ cyclo-alkenyl; or $C_{6-10}$ aryl; or aralkyl; or aralkenyl; or aralkynyl; or cycloalkylkenyl; or a monocyclic or polycyclic, saturated or unsaturated heterocyclic group containing from 1 to 4 of any one or more of the heteroatoms N, S, or O in each heterocyclic ring; or a fused polycyclic saturated or unsaturated heterocyclic group containing from 1 to 4 of any one or more of the heteroatoms N, S, or O in each heterocyclic ring; or heterocyclylalkenyl; or heterocyclylalkynyl; wherein the heterocyclyl, alkyl, alkenyl, and alkynyl groups are as defined above; wherein each of the above organic radicals is unsubstituted or substituted by one or more atoms or groups selected from chloro, bromo, fluoro, cyano, azido, nitro, formyl, $C_{1-4}$ alkyl, trifluoromethyl, $C_{2-4}$ alkenyl, $C_{2-4}$ alkynyl, $C_{3-6}$ cycloalkyl, hydroxy, alkoxy, carboxy, $—(CH_2)_mCOOR_{10}$, $—COR_{10}$, $—COCF_3$, $—CONH_2$, $—CONHR_{10}$, $—NH_2$, $—NHR_{10}$, $—NR_{10}R_{11}$, $—NHSO_2R_{10}$, $—NHCOR_{10}$, $—NHC(=NH)NH_2$, $—OCOR_{10}$, $—OC(O)NH_2$, $—SH$, $—SR_{10}$, $—S(O)R_{10}$, $—S(O)2R_{10}$, and $—SO_3$ H;

$R_2$ is selected from hydrogen; or chloro, bromo, or fluoro; or $—C_{1-6}$ alkyl; or -trifluoromethyl; or $—C_{2-6}$ alkenyl (substituted or unsubstituted); or $—C_{2-6}$ alkynyl (substituted or unsubstituted); or $—C_{3-8}$ cycloalkyl, or $—OR_7$; or $—S(O)nR_7$; or $—CHO$; or $—COOH$; or $—CH_2—O—R_7$; or $—CH_2—S(O)_nR_7$; or $—C(O)R_7$; or $—C(O)OR_7$; or $—CH_2OC(O)R_7$; or $—CH_2SC(O)R_7$; or $—CH_2Cl$; or $—CH_2Br$; or $—CH_2OC(O)NH_2$; or $—CH_2NR_7R_8$; or $—CH_2—NH(C_{1-4}$ alkyl), wherein the alkyl is either unsubstituted or substituted; or $—CH_2—NHC(O)R_7$; or $—CH_2—N^{\oplus}R_7R_8R_9$; or $—CH_2—S(O)_nHet$;

$R_3$ and $R_4$ are the same or different and may be hydrogen; or $C_{1-6}$ straight or branched alkyl group; or $C_{6-10}$ aryl group; or $C_{3-8}$ cycloalkyl group; or aralkyl group; or saturated or unsaturated monocyclic or fused polycyclic 3–8 membered heterocyclic group containing at least one heteroatom chosen from O, S, and N; or a halogenated $C_{1-6}$ alkyl; or a hydroxy $C_{1-6}$ alkyl; or $—CH_2COOH$; or $—COOH$; or $—COOC_{1-6}$ alkyl group; or $—CH_2COOC_{1-6}$ alkyl;

$R_5$ is $R_1$; or $—O—R_1$; or $—S(O)_nR_1$; $—OC(O)R_1$; $—OSO_2R_1$; or $—NHC(O)R_1$; or $—NH—Z$; or halogen;

$R_6$ is hydrogen; or $C_{1-4}$ alkyl; or $C_{1-4}$ alkoxy; or halogen;

$R_7$, $R_8$ and $R_9$ are the same or different, and may be hydrogen; or $C_{1-6}$ lower straight or branched alkyl; or $C_{2-6}$ alkenyl; or $C_{2-6}$ alkynyl; or $C_{3-8}$ cycloalkyl; or $C_{6-10}$ aryl; or aralkyl; or saturated or unsaturated monocyclic or fused polycyclic 3 to 8 membered heterocyclic ring containing at least one heteroatom chosen from O, S, and N; or, at least two of them, taken together with the nitrogen atom to which they are attached, form a heterocyclic ring;

$R_{10}$ and $R_{11}$ may be the same or different and represent $C_{1-6}$ straight or branched alkyl, phenyl, or benzyl;

Z is hydrogen; a mono-peptide composed of D or L -amino acids with the terminal amino group optionally acylated by —C(O)$R_1$ or —C(O)O$R_1$; or a di-peptide composed of D or L -amino acids with the terminal amino group optionally acylated by —C(O)$R_1$ or —C(O)O$R_1$; or a tripeptide composed of D or L -amino acids with the terminal amino group optionally acylated by —C(O)$R_1$ or —C(O)O$R_1$;

Het is a heterocyclic ring;

m is 0, 1, 2 and 3; and n is 0, 1, or 2.

In another aspect, the present invention relates to a process for preparing a compound of formula (I) as defined above comprising:

i) providing a compound having the formula (II)

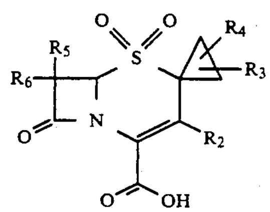

ii) converting the carboxyl group at the 4-position of the cephem nucleus of the formula (II) into an activated acid derivative having the formula (III)

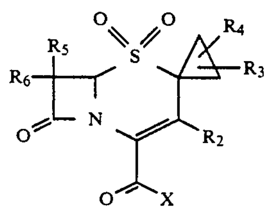

iii) treating the activated acid derivative of formula (III) with an organometallic derivative of $R_1$ to provide a compound having the formula (I).

In another aspect, the present invention relates to an alternative process for preparing a compound of Formula (I), comprising:

i) providing a compound having the formula (IV)

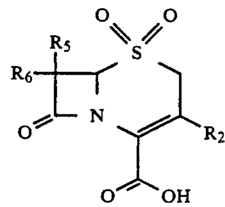

ii) converting the carboxyl group at the 4-position of the cephem nucleus of formula (IV) into an activated acid derivative having the formula (V)

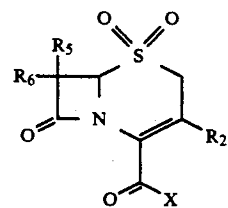

iii) treating the activated acid derivative of formula (V) with an organometallic derivative of $R_1$ to provide a compound of the formula (VI)

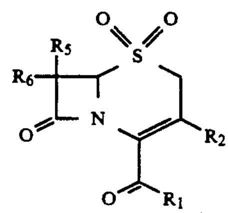

iv) aminomethylating the compound of formula (VI) to provide a compound having the formula (VII)

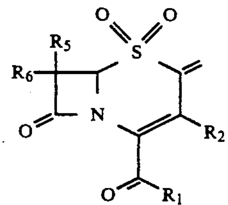

v) carrying out a cycloaddition reaction to the compound of formula (VII) with $R_3R_4CN_2$ to provide a compound of the formula (I).

DETAILED DESCRIPTION OF THE PREFERRED EMBODIMENTS

As summarized above, the present invention relates to 2-spirocyclopropyl 4-acylcephem sulfones which are potent elastase inhibitors, their preparation and to pharmaceutical and veterinary compositions containing them.

More specifically, a 2-spirocyclopropyl 4-acylcephem sulfone of the structural formula (I) is provided:

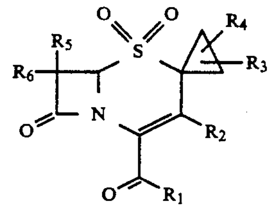

wherein $R_1$ in formula (I) represents a hydrogen atom; $C_{1-12}$ straight or branched alkyl; $C_{2-10}$ alkenyl; $C_{2-10}$ alkynyl; $C_{3-8}$ cycloalkyl; $C_{5-8}$ cycloalkenyl; $C_{6-10}$ aryl; aralkyl; aralkenyl; aralkynyl; (cycloalkyl) alkyl; a monocyclic or fused polycyclic, saturated or unsaturated heterocyclic group containing from 1 to 4 of any one or more of the heteroatoms N, S or O in each heterocyclic ring; heterocyclylalkyl; heterocyclylalkenyl;

heterocyclylalkynyl, wherein the heterocyclyl, alkyl, alkenyl, and alkynyl groups are as defined above; wherein each of the above organic radicals is unsubstituted or substituted by one or more atoms or groups selected from halogen; cyano; azido; nitro; formyl; $C_{1-4}$ alkyl; trifluoromethyl; $C_{2-4}$ alkenyl; $C_{2-4}$ alkynyl; $C_{3-6}$ cycloalkyl; hydroxy or alkoxy; carboxy; —$(CH_2)_m$COOH or —$(CH_2)_m$$COOR_{10}$; —$COR_{10}$ or —$COCF_3$; —$CONH_2$, —$CONHR_{10}$ or N—(carboxymethyl) carbamoyl (—$CONHCH_2COOH$); or —$NH_2$, —$NHR_{10}$ or —$NR_{10}R_{11}$; —$NHSO_2R_{10}$; —$NHCOR_{10}$; —NHC(=NH)$NH_2$; —$OCOR_{10}$; —OC(O)$NH_2$; or —SH or —$SR_{10}$; —S(O)$R_{10}$; —$S(O)_2R_{10}$; —$SO_3H$; mono-, di-, or tri-substituted halomethyl, aminomethyl, hydroxymethyl, and cyanomethyl; wherein m is 0, 1, 2, and 3; $R_{10}$ and $R_{11}$ may be the same or different and represent $C_{1-6}$ straight or branched alkyl, phenyl, or benzyl.

The preferred groups representing $R_1$ include methyl, ethyl, n-propyl, iso-propyl, n-butyl, iso-butyl, tert-butyl, neo-pentyl, cyclopropyl, cyclobutyl, cyclopentyl, cyclcohexyl, cycloheptyl, cyclopentenyl, cyclohexenyl, ethenyl, propenyl, ethynyl, phenyl, benzyl, thiazolyl, thiadiazolyl, triazolyl, tetrazolyl, triazinyl, pyrolyl, imidazolyl, furyl, thienyl, pyridyl and pyrimidinyl. Of these, the most preferred groups representing $R_1$ are hydrogen, methyl, ethyl, butyl, tert-butyl, neo-pentyl, cyclopropyl, phenyl, benzyl, dimethylphenyl, diphenylmethyl and propenyl.

$R_2$ in the formula (I) may be selected from hydrogen, chloro, bromo or fluoro, $C_{1-6}$ alkyl, trifluoromethyl, Optionally substituted $C_{2-6}$ alkenyl, optionally substituted $C_{2-6}$ alkynyl, $C_{3-8}$ cycloalkyl, —$OR_7$, —$S(O)_nR_7$, —CHO, —COOH, —C(O)$R_7$, —C(O)$OR_7$, —$CH_2$—O—$R_7$, —$CH_2$—$S(O)_nR_7$, —$CH_2OC(O)R_7$, —$CH_2SC(O)R_7$, chloromethyl, bromomethyl, —$CH_2OC(O)NH_2$, —$CH_2NR_7R_8$, wherein $R_7$ and $R_8$ may be the same or different; $R_7$ and $R_8$ taken together with the nitrogen atom may represent a heterocyclic ring. Some representative examples include:

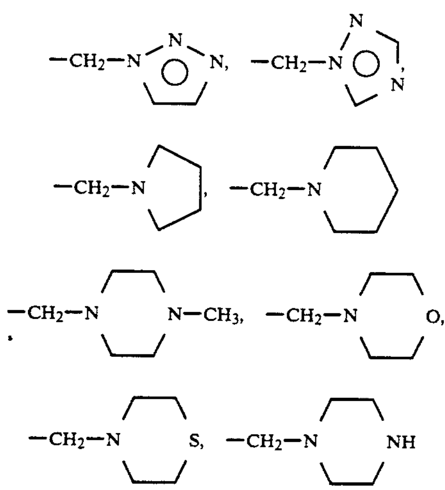

$R_2$ may also be a quaternary ammonium group —$CH_2$—$N^{\oplus}R_7R_8R_9$, wherein $R_7$ and $R_8$ may be the same or different; $R_7$ and $R_8$ taken together with the nitrogen atom may represent a heterocyclic ring. $R_8$ and $R_9$ may be the same or different; $R_8$ and $R_9$ taken together with the nitrogen atom may represent a heterocyclic ring. $R_7$ and $R_9$ may be the same or different. $R_7$ and $R_9$ taken together with the nitrogen atom may represent a heterocyclic ring. $R_7$, $R_8$ and $R_9$ taken together with the nitrogen atom to which they are attached may represent an aromatic heterocyclic ring. Some representative examples include:

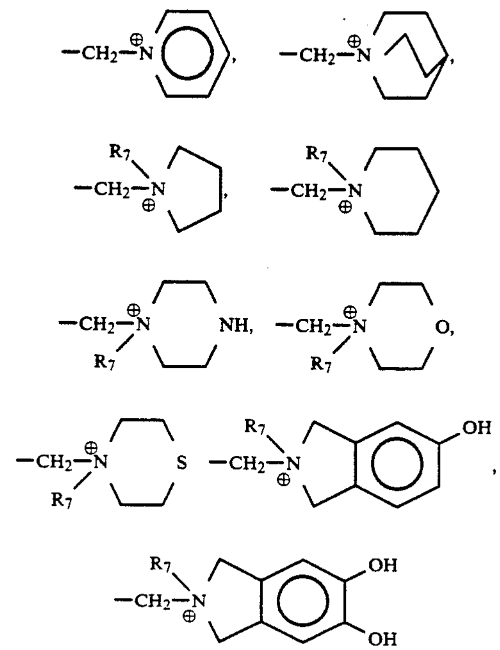

wherein $R_7$ is hydrogen, $C_{1-6}$ lower straight or branched alkyl, $C_{2-6}$ alkenyl, $C_{2-6}$ alkynyl, $C_{3-8}$ cycloalkyl, $C_{6-10}$ aryl, aralkyl, aralkenyl, aralkynyl, heterocyclyl ring and heterocyclylalkyl;

$R_8$ is $R_7$;

$R_9$ is $R_7$;

"heterocyclyl" is a saturated or unsaturated monocyclic or fused polycyclic 3–8 membered heterocyclic group containing at least one heteroatom chosen from O, S and N;

and n is either 0, 1 or 2.

$R_2$ may also be NH—Z, wherein Z is hydrogen, a mono, di- or tripeptide composed of D or L $\alpha$-aminoacids with the terminal amino group either free or acylated by —C(O)$R_1$ or —C(O)$OR_1$; —$CH_2$—NH—C(O)$R_7$; —$CH_2$—$S(O)_n$Het, wherein n is either 0, 1 or 2 and Het is a heterocyclic ring. Het is preferably selected from:

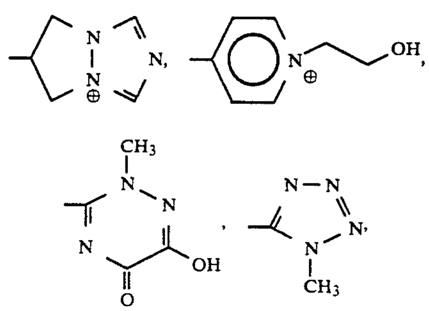

-continued

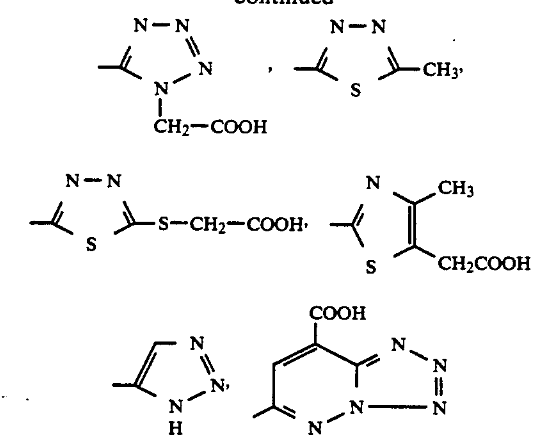

The preferred groups representing $R_2$ include hydrogen; chloro; methyl; trifluoromethyl; hydroxy; methoxy; ethoxy; vinyl; cyclopropyl; acetoxymethyl; hydroxymethyl; chloromethyl; bromomethyl; carbamoyloxymethyl; methylthio; formyl; acetyl; benzoyl; carboxy; methoxycarbonyl; ethoxycarbonyl; tert-butoxycarbonyl; methoxymethyl; ethoxymethyl; isopropoxymethyl; phenoxymethyl; 3-pyridyloxymethyl, wherein the phenyl and pyridyl rings may be unsubstituted or substituted by one or two similar or two different groups selected from hydroxy, carboxy, amino, and $C_{1-4}$ alkoxycarbonyl; methylthiomethyl; methylsulphonylmethyl; phenylthiomethyl; phenylsulphonylmethyl; (1,2,3-triazol-1-yl)methyl; (1,2,4-triazol-1-yl)methyl; acetylthiomethyl; aminomethyl; $—CH_2—NH$ ($C_{1-4}$ alkyl), wherein the alkyl group is either unsubstituted or substituted, preferably by a carboxy group; trialkyl-ammonium methyl group wherein the alkyl group is selected from methyl, ethyl and propyl; alkyl (cycloalkyl) ammonium methyl, preferably selected from:

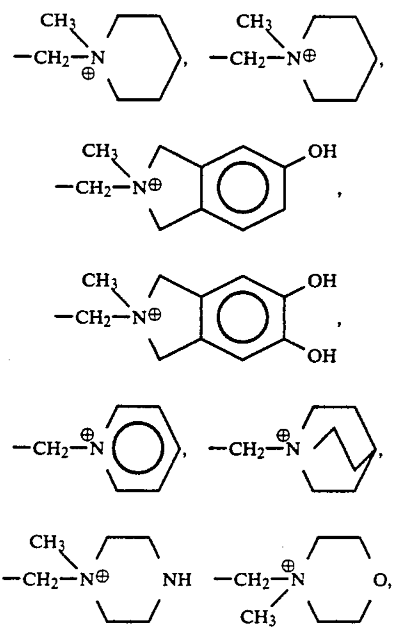

-continued

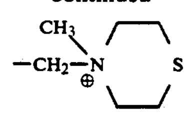

$R_2$ may also preferably be $—CH_2—S(O)_nHet$, wherein Het is a heterocyclic ring preferably selected from

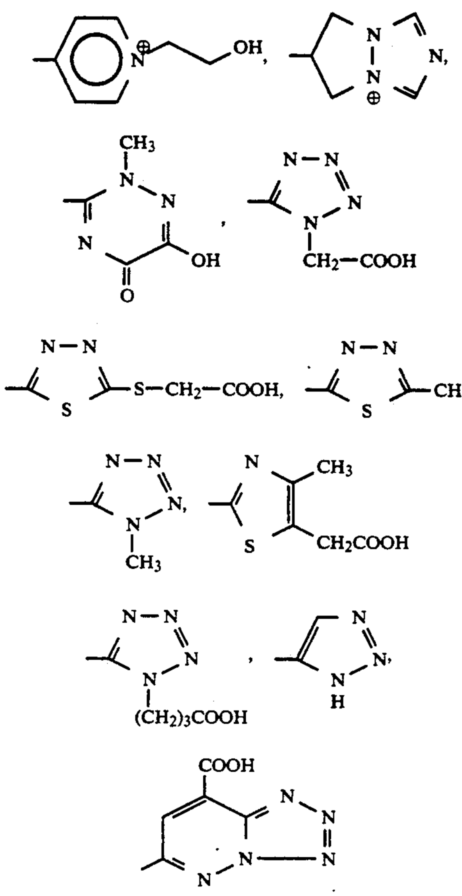

The most preferred groups representing $R_2$ include hydrogen, chloro, methyl, trifluoromethyl, hydroxy, methoxy, vinyl, cyclopropyl, methylthio, acetoxymethyl, hydroxymethyl, chloromethyl, bromomethyl, carbamoyloxymethyl, methoxymethyl, phenoxymethyl, 3-pyridyloxymethyl, methylthiomethyl, methylsulfonylmethyl, phenylthiomethyl, phenylsulfonylmethyl, (1,2,3-triazol-1-yl)methyl, (1,2,4-triazol-1-yl)methyl, acylthiomethyl, aminomethyl, a quaternary ammonium methyl group selected from:

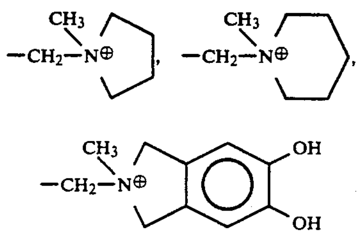

-continued

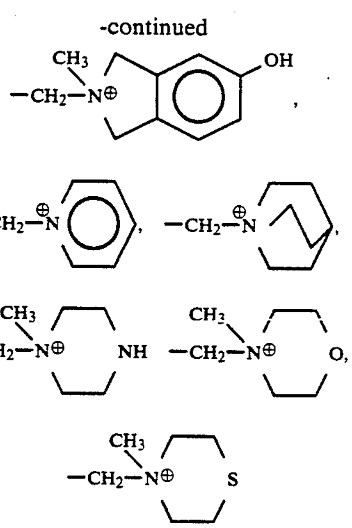

$R_2$ is also most preferably selected from the group consisting of $CH_2$—$S(O)_n$ Het, wherein n is 0, 1 or 2 and Het is a heterocyclic ring selected from:

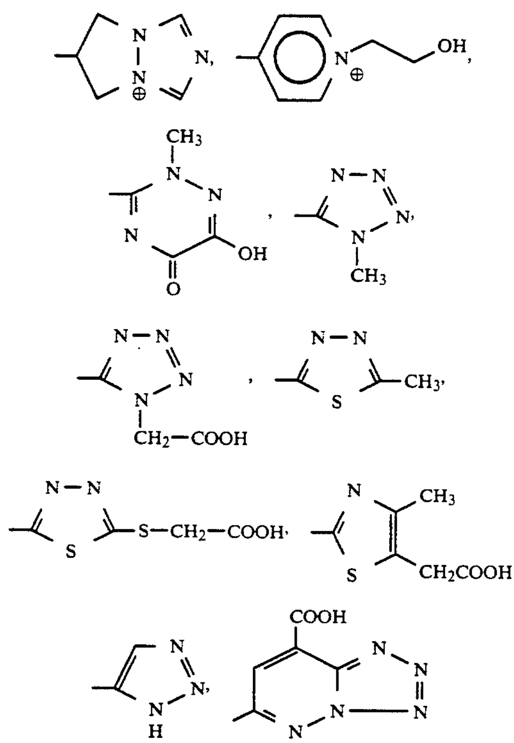

$R_3$ and $R_4$ in the formula (I) may be the same or different and are selected from hydrogen, $C_{1-6}$ straight or branched alkyl group, $C_{6-10}$ aryl group, $C_{3-8}$ cycloalkyl group, aralkyl group, saturated or unsaturated monocyclic or fused polycyclic 3 to 8 membered heterocyclic group containing at least one heteroatom selected from O, S and N; heteroarylalkyl group, —COOH, —$CH_2COOH$, —$COOC_{1-6}$ alkyl, and —$CH_2COOC_{1-6}$ alkyl.

The above groups can be further substituted with one or more groups such as alkyl, hydroxy, halogen, amino, carboxy, cyano, haloalkyl, carboxamido, sulfinyl and sulfonyl.

$R_3$ and $R_4$ are preferably selected from hydrogen, methyl, ethyl, t-butyl, isopropyl, chloromethyl, fluoromethyl, cyclopropyl, phenyl, p-chlorophenyl, p-fluorophenyl, trifluoromethyl, 2-pyridylmethyl, 2-thienylmethyl, pyridyl, thienyl, furyl, —COOH, —$CH_2COOH$, —$CH_2COOCH_3$, and —$CH_2COOCH_2CH_3$, with hydrogen, methyl, trifluoromethyl, cyclopropyl, t-butyl, phenyl, p-chlorophenyl, p-fluorophenyl, thienyl, furyl, pyridyl, —COOH, —$CH_2COOH$, —$CH_2COOCH_3$, and —$CH_2COOCH_2CH_3$ being most preferred.

The partial structure represented by the formula:

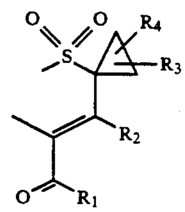

is to be understood to include both position isomers as represented by the following formulae:

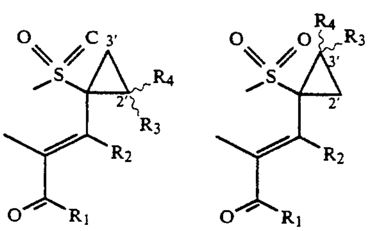

Furthermore it should be noted that when $R_3$ and $R_4$ in formula (I) are different they may be present in the form of an optical isomer, for example, l,d- or dl- forms.

$R_5$ in the formula (I) is hydrogen, chloro, fluoro, bromo or iodo, $R_1$, —$OR_1$, —$S(O)_nR_1$ wherein n is either 0, 1 or 2, —$OC(O)R_1$, —$OSO_2R_1$, —$NHC(O)R_1$, —NH—Z, wherein Z is hydrogen, a mono-, di- or tripeptide composed of D or L α-amino acids with the terminal amino group either free or acylated by —$C(O)R_1$ or —$C(O)OR_1$.

$R_5$ is preferably selected from hydrogen, chloro, fluoro, bromo, methoxy, ethoxy, methyl, ethyl, formamido, acetamido, trifluoroacetamido, acetyloxy, chloroacetyloxy, bromoacetyloxy, dichloroacetyloxy, methylsulfonyloxy, phenylsulfonyloxy, and tolylsulfonyloxy, with hydrogen, chloro, bromo, fluoro, methyl, ethyl, methoxy, ethoxy, methylsulfonyloxy, acetyloxy, and acetamido being most preferred.

$R_6$ in formula (I) is selected from hydrogen, chloro, bromo, methoxy, and methylthio. The compounds of the present invention can be prepared by a process which comprises the following steps:

(i) providing a compound having the formula (II)

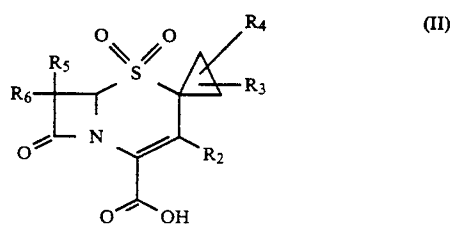

(II)

(ii) converting the carboxyl group —COOH at 4-position of the cephem nucleus of the formula (II) into an activated acid derivative having the formula (III)

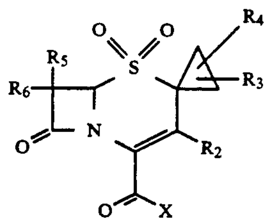

(iii) treating the activated acid derivative (for example, acid chloride) of formula (III) with an organometallic derivative of $R_1$ to provide a compound having the formula (I).

The carboxylic acid group is typically activated as the acyl halide, anhydride, mixed anhydride, thioester, etc.

The preferred organometallic derivatives of $R_1$ include Grignard reagents ($R_1MgX$), organolithium reagents ($R_1Li$), lithium dialkylcopper reagents [$(R_1)_2CuLi$)], organocadmium reagents [$(R_1)_2Cd$)], organozinc reagents (RlZnBr), and cuprous reagents ($R_1Cu$ e.g. cuprous acetylides). Still other suitable reagents include organomanganese compounds, organotin reagents, lithium aryltrialkylborates, bis(triphenylphosphine)carbonylalkylrhodium(I), a magnesium dialkylcopper reagent ($R_1CH_3CuMgX$), and $PhS(R_1)CuLi$. Certain metallic halides, notably ferric and cuprous halides and $AlX_3$, may be used as catalysts to improve the yields.

Alternatively, the compounds of the present invention can be prepared by a process which comprises the following steps:

(iv) providing a compound having the formula (IV)

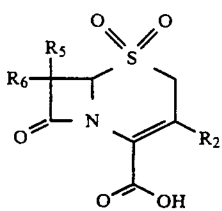

(v) converting the carboxy group at 4-position of the cephem nucleus of formula (IV) into an activated acid derivative of the formula (V)

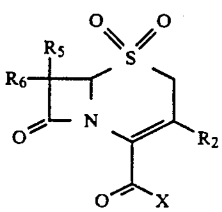

(vi) treating the activated acid derivative of formula (V) with an organometallic derivative of $R_1$ to provide a compound of the formula (VI)

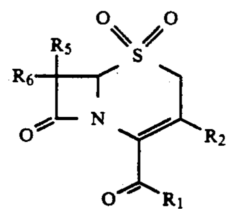

(vii) aminomethylating the compound of formula (VI) to provide a compound having the formula (VII); and

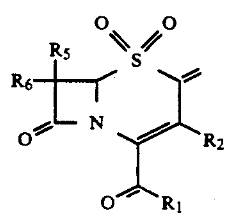

(viii) carrying out a cycloaddition reaction to the compound of formula (VII) with $R_3R_4CN_2$ to provide a compound of the formula (I).

The carboxyl group of compound (II) or compound (IV) can be converted to a suitable reactive derivative according to the conventional methods described in the cephalosporin or penicillin literature. For example, the carboxylic acid group can be converted to an acid halide by treatment with a halogenating agent such as phosphorus oxychloride, thionyl chloride, phosphorus pentachloride, oxalyl chloride, or oxalyl bromide. The reactions are usually carried out in a conventional solvent such as acetone, dioxane, acetonitrile, chloroform, methylene chloride, ethylene chloride, tetrahydrofuran, ethyl acetate, N, N-dimethyl formamide or any other organic solvent which does not adversely influence the reaction.

The present reaction is preferably carried out under mild conditions such as under cooling, at ambient, or slightly elevated temperature.

The reactions of activated acid derivatives of formula (III) and (V) with organometallic reagents can be carried out according to the conditions described in "Advanced Organic Chemistry", J. March, McGraw-Hill, incorporated herein by reference. The reactions are usually carried out in an inert solvent like ether, hexane, tetrahydrofuran and the like. The reaction is usually carried out at a low temperature, preferably between −78° to 10° C. The introduction of an exocyclic double bond at the position of compound (VI) can be carried out according to the procedure detailed in I. G. Wright et al., *J. Med. Chem.*, 14, 420 (1971), incorporated herein by reference. The reaction is usually carried out in a solvent such as tert-butanol, methylene chloride, chloroform, carbon tetrachloride, dioxane, a mixed solvent thereof, or any other solvent which does not adversely affect the reaction. There is no particular limitation to the reaction temperature and the present reaction is usually carried out from room temperature to about 150° C. with or without reflux until the reaction is complete.

The introduction of 2-spirocyclopropyl groups, which may be substituted with suitable substituents, may be performed by reacting the compound (VII)

with a compound of the formula $R_3R_4CN_2$ wherein $R_3$ and $R_4$ may be the same or different and represent the groups as defined before. The reaction is usually carried out in a solvent such as methylene chloride, chloroform, carbon tetrachloride, benzene, ether, ethyl acetate, or any other solvent which does not adversely affect the reaction. The reaction is usually carried out under cooling to ambient temperature.

The most preferred embodiments of the present invention include the following compounds:

7α-methoxy-2-spiro(2',2'-diphenyl)cyclopropyl-3-methyl-3-cephem-4-ethylcarbonyl 1,1-dioxide;
7α-methoxy-2-spiro(2',2'-diphenyl)cyclopropyl-3-methyl-3-cephem-4-butylcarbonyl 1,1-dioxide;
7α-methoxy-2-spiro(2',2'-diphenyl)cyclopropyl-3-methyl-3-cephem-4-methylcarbonyl 1,1-dioxide;
7α-methoxy-2-spiro(2',2'-diphenyl)cyclopropyl-3-methyl-3-cephem-4-phenylcarbonyl 1,1-dioxide;
7α-methoxy-2-spiro(2',2'-diphenyl)cyclopropyl-3-methyl-3-cephem-4-tert-butylcarbonyl 1,1-dioxide;
7α-chloro-2-spiro(2',2'-diphenyl)cyclopropyl-3-methyl-3-cephem-4-phenylcarbonyl 1,1-dioxide; and
7α-chloro-2-spiro(2',2'-diphenyl)cyclopropyl-3-methyl-3-cephem-4-tert-butylcarbonyl 1,1-dioxide.

The compounds of the present invention are characterized by high inhibitory activity on HLE. The in vitro test data on anti-elastase activity of exemplary derivatives having the formula (I) are shown in the Table.

TABLE

Activity of 2-spirocyclopropyl 4-acylcephem sulphones against human leukocyte elastase (HLE).

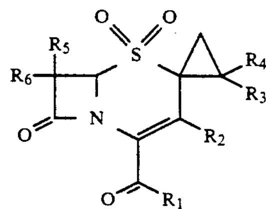

| Compd | $R_1$ | $R_2$ | $R_3$ | $R_4$ | $R_5$ | $R_6$ | $IC_{50}$, nM |
|---|---|---|---|---|---|---|---|
| 1 | $CH_3$ | $CH_3$ | Ph | Ph | $CH_3O$ | H | |
| 2 | $CH_2CH_3$ | $CH_3$ | Ph | Ph | $CH_3O$ | H | 10.3 |
| 3 | $Bu^n$ | $CH_3$ | Ph | Ph | $CH_3O$ | H | 7.4 |
| 4 | Ph | $CH_3$ | Ph | Ph | Cl | H | 8.9 |
| 5 | $Bu^t$ | $CH_3$ | Ph | Ph | Cl | H | 6.3 |
| 6 | $Bu^t$ | $CH_3$ | Ph | Ph | $CH_3O$ | H | 12.0 |

Owing to their high anti-elastase activity and quite negligible toxicity, the compounds of the present invention can be used in the treatment of inflammatory or degenerative diseases caused by proteolytic enzymes in mammals, including humans. The compounds of the present invention may be administered to a warm-blooded mammalian in need thereof, particularly a human, to prevent or arrest the progression of diseases such as emphysema, pulmonary emphysema, lupus, rheumatoid arthritis, osteoarthritis, cystic fibrosis, spondylitis, gout, psoriasis, chronic bronchitis, and acute respiratory distress syndrome caused by proteolytic degradation of lungs and other connective tissues.

The mode of administration may be oral, parenteral, topical, rectal or by inhalation. The compounds may be conventionally formulated in an oral or parenteral dosage form by compounding about 10 to 250 mg per unit of dosage with conventional vehicle excipients, binders, preservatives, stabilizers, flavoring agents, coloring agents, and sweetening agents or the like as called for by accepted pharmaceutical or veterinary practice.

For parenteral administration, a 1 to 10 ml intravenous, intramascular or subcutaneous injection would be given containing about 0 02 to 10 mg/kg of body weight of a compound of the present invention three to four times daily. The injection would contain a compound of the present invention in an aqueous isotonic sterile solution or suspension, optionally with a preservative such as phenol or a solubilizing agent such as ethylenediaminetetraacetic acid (EDTA). Among the acceptable vehicles and solvents that may be employed are water, Ringer's solution and isotonic sodium chloride solution. In addition, sterile, fixed oils are conventionally employed as a solvent or suspending medium. Synthetic monoglycerides, diglycerides, and fatty acids such as oleic acid find use as fixed oil in the preparation of injectables.

For rectal administration, the compounds of the present invention can be prepared in the form of suppositories by mixing with a suitable non-irritating excipient such as cocoa butter or polyethylene glycols.

For topical use, the compounds of the present invention can be prepared in the form of ointments, jellies, solutions or suspensions.

The compounds of the invention may be administered as a powdered aerosol by a Spinhaler turbo-inhaler device commercially available from Fisons Corp. of Bedford, Massachusetts at a rate of about 0.1 to 50 mg per capsule, 1 to 8 capsules being administered daily for an average human. In a liquid aerosol, the compounds of the present invention are administered at the rate of about 100 to 1000 micrograms per "puff" or activated release of a standard volume of propellant. The liquid aerosol would be given at the rate of 1 to 8 puffs per day with variation in dosages due to the severity of the condition being treated, the weight of the patient and the particle size distribution of the aerosol. A fluorinated hydrocarbon or isobutane may find use as propellants for liquid aerosols.

Daily dose are in the range of about 0.01 to about 100 mg per kg of body weight, depending on the activity of the specific compound, the age, weight, sex and condition of the subject to be treated, the type and severity of the disease, and the frequency and route of admistration. The amount of active in gradient that may be combined with the carrier materials to produce a single dosage will vary depending upon the host treated and the particular mode of administration.

EXAMPLES

Example 1

7α-Methoxy-2-spiro (2',2'-diphenyl)cyclopropyl-3-methyl-3-cephem-4-ethylcarbonyl 1,1-dioxide To a suspension of 7α-methoxy-2-spiro(2',2'-diphenyl)cyclopropyl-3-methyl-3-cephem-4-carboxylic acid 1,1-dioxide (360 mg, 0.8191 mmol) in dry methylene chloride (15 ml) cooled in an ice-bath was added oxalyl chloride (135 mg, 1.065 mmol) followed by one drop of dimethyl formamide. The mixture slowly went into solution (still some solid left). After 5 min another drop of dimethyl formamide was added, ice-bath was removed and the reaction mixture went into solution completely within 10 min; the mixture was stirred at room temperature for 40 min, solvent was removed under reduced pressure. The residue was dissolved in dry THF (10 ml), cooled to −70° C., cuprous iodide (164 mg, 0.8601 mmol) was added followed by ethyl magnesium bromide [0.532 ml, 2 (M) solution in THF] and the reaction mixture was stirred at −70° C. for 15 min; poured into ice-cold water, extracted with methylene chloride, washed with aqueous sodium bicarbonate solution, brine, dried and concentrated to give a light yellow solid which was purified over a silica gel column using hexane-ethyl acetate (7:3) as eluant, 190 mg.

Crystallization from methylene chloride-ether gave pure white solid, m.p. 206°–208° C., decomp. IR(KBR)ν1777, 1695, 1617 cm-$^{-1}$.

$^1$H NMR (200 MHZ, $CDCl_3$): δ0.975 (s, 3H, $CH_3$), 1.19 (t, 3H, $CH_2CH_3$), 2.34 (d, 1H, J=7.1 Hz, cyclopropyl), 2.67 (dq, 1H, $\underline{CH_2}CH_3$), 2.97 (dq, 1H, $\underline{CH_2}CH_3$), 2.94 (d, 1H, J=7.1 Hz, cyclopropyl), 3.48 (s, 3H, $OCH_3$), 4.97 (d, 1H, J=1.7 Hz), 5.05 (d, 1H, J=1.7 Hz), 7.18–7.49 (m, 10H, aromatic).

Example 2

7α-Methoxy-2-spiro(2′,2′-diphenyl)cyclopropyl-3-methyl-3-cephem-4-butylcarbonyl 1,1-dioxide To a suspension of 7α-methoxy-2-spiro(2′,2′-diphenyl)cyclopropyl-3-methyl-3-cephem-4-carboxylic acid 1,1-dioxide (700 mg, 1.5928 mmol) in dry DCM (25 ml) cooled in an icebath was added oxalyl chloride (263 mg, 2.0706 mmol) followed by two drops of N,N-dimethylformamide, the reaction mixture was stirred at ice-temperature for 15 minutes and then at room temperature for 45 min; solvent was removed under reduced pressure. The residue was dissolved in dry THF (15 ml), cooled to −70° C., cuprous iodide (319 mg, 1.6724 mmol) was added followed by n-butyl magnesium chloride (1 035 ml, 2 (M) in THF) and the reaction mixture was stirred at −70° C. for 15 min; poured into ice-cold water, extracted with methylene chloride, the aqueous layer was saturated with sodium chloride and re-extracted with methylene chloride. The combined organic layers were washed with aqueous sodium bicarbonate solution, brine, dried and concentrated to give a light yellow foam (600 mg) which was purified over a silica gel column using hexane-ethyl acetate mixture as eluant (520 mg).

Crystallization from methylene chloride-ether gave pure compound as white crystals, m.p. 170°–175° C. IR (KBr) ν1779, 1694, 1609 cm$^{-1}$.

$^1$H NMR (200 MHz, $CDCl_3$): δ0.98 (s, 3H, $CH_3$), 0.98 (t, 3H, $CH_3$), 1.33–1.72 (m, 4H), 2.34 (d, 1H, J=6.8 Hz, cyclopropyl), 2.73–2.95 (m, 2H, —$COCH_2$—), 2.93 (d, 1H, J=6.8 Hz, cyclopropyl), 3.49 (s, 3H, $OCH_3$), 4.97 (d, 1H, J=2.0 Hz), 5.04 (d, 1H, J=2.0 Hz), 7.22–7.48 (m, 10H, aromatic).

Example 3

7α-Methoxy-2-spiro(2′,2′-diphenyl)cyclopropyl-3-methyl-3-cephem-4-methylcarbonyl 1,1-dioxide To a suspension of 7α-methoxy-2-spiro (2′,2′-diphenyl) cyclopropyl-3-methyl-3-cephem-4-carboxylic acid 1,1-dioxide (500 mg, 1.138 mmol) in dry methylene chloride (18 ml) cooled to 0° C., was added oxalyl chloride (188 mg, 1.479 mmol) followed by two drops of DMF. The mixture was stirred at ice-temperature for 15 min and then at room temperature for 45 min; solvent was removed under reduced pressure. The residue was redissolved in dry THF (I0 ml), cooled to −70° C., cuprous iodide (228 mg, 1.195 mmol) was added followed by methyl magnesium bromide (0.49 ml, 3(M) in ether) and the reaction mixture was stirred at −70° C. for 15 min; poured into ice-cold water, extracted with methylene chloride, washed with aqueous sodium bicarbonate solution, brine, dried and concentrated to give a light yellow foam (300 mg) which was purified over silica gel column using hexane-ethyl acetate (3:1) as eluant to give pure compound (150 mg) which was crystallized from methylene chloride-ether (88 mg), m.p. 196°–198° C., decomp. IR (KBr) ν1778, 1695, 1594 cm$^{-1}$.

$^1$H NMR(200 MHz, $CDCl_3$):δ1.02 (s, 3H, $CH_3$), 2.35 (d, 1H, J =6.84 Hz), 2.52 (s, 3H, $CO\underline{C}H_3$), 2.95 (d, 1H, J=7.2 Hz), 3.49 (s, 3H, $OCH_3$) , 4.98 (d, 1H, J=1.59 Hz), 5.05 (d, 1H, J=1.94 Hz), 7.22–7.49 (m, 10H, aromatic).

Example 4

7α-Methoxy-2-spiro(2′,2′-diphenyl)cyclopropyl-3-methyl-3-cephem-4-phenylcarbonyl 1,1-dioxide To a suspension of 7α-methoxy-2-spiro(2′,2′-diphenyl)cyclopropyl- 3-methyl-3-cephem-4-carboxylic acid 1,1-dioxide (500 mg, 1.138 mmol) in dry methylene chloride (18 ml) cooled to 0° C., was added oxalyl chloride (188 mg, 1.479 mmol) followed by two drops of DMF. The mixture was stirred at 0° C. for 15 min and then at room temperature for 45 min; solvent was removed under reduced pressure. The residue was redissolved in dry THF (10 ml), cooled to −70° C., cuprous iodide (228 mg, 1 195 mmol) was added followed by phenyl magnesium bromide (1.48 ml, 1(M) in THF) and the reaction mixture was stirred at −70° C. for 15 min; poured into ice-cold water, extracted with methylene chloride, washed with aqueous sodium bicarbonate solution, brine, dried and concentrated to give a light yellow foam (370 mg) which was purified over a silica gel column using hexane-ethyl acetate mixture (3:1) as eluant to give the desired compound (80 mg). Crystallization from methylene chloride - ether afforded shiny crystals (36 mg), mp. 180°–182° C., decomp. IR (KBr) δ1786, 1594 cm$^{-1}$.

$^1$H NMR($CDCl_3$): δ1.11 (s, 3H, $CH_3$), 2.414 (d, 1H, J=7.2 Hz), 3.02 (d, 1H, J=7.2 Hz), 3.52 (s, 3H, $OCH_3$), 5.02 (d, 1H, J=1.42 Hz), 5.10 (d, 1H, J=1.48 Hz), 7.26–7.50 (m, 15H, aromatic).

Example 5

7α-Methoxy-2-spiro(2′,2′-diphenyl)cyclopropyl-3-methyl-3-cephem-4-t-butylcarbonyl 1,1-dioxide To a suspension of 7α-methoxy-2-spiro(2′,2′-diphenyl) cyclopropyl-3-methyl-3-cephem-4-carboxylic acid 1,1-dioxide (300 mg, 0.6826 mmol) in dry methylene chloride (10 ml) cooled to 0° C., was added oxalyl chloride (113 mg, 0.8874 mmol) followed by two drops of DMF. The mixture was stirred at 0° C. for 15 min and then at room temperature for 45 min; solvent was removed under reduced pressure. The residue was redissolved in dry THF (5 ml), cooled to −70° C., cuprous iodide (136 mg, 0.71677 mmol) was added followed by t-butyl magnesium chloride (0.44 ml, 0.8874 mmol, 2.0 (M) in THF) and the reaction mixture was stirred at at −70° C. for 15 min; poured into ice-cold water, extracted with methylene chloride, washed with aqueous sodium bicarbonate solution, dried and concentrated to give a crude product (250 mg) which was purified over a silica gel column using hexane-ethyl acetate mixture as the eluant. The product (122 mg) obtained was repurified over a silica column using 5% ethyl acetate in methylene chloride. The product (45 mg) obtained on treatment with ether gave a white solid (25 mg) which was crystallized from methylene chloride-ether, m.p. 222° C., decomp. IR (KBr) ν1779; 1685, 1610 $cm^{-1}$.

$^1H$ NMR (200 MHz, $CDCl_3$): δ0.873 (s, 3H, $CH_3$), 1.2969 (s, 9H, $Bu^t$), 2.32 (d, 1H, J=6.8 Hz), 2.88 (d, 1H, J=6.8 Hz), 3.48 (s, 3H, $OCH_3$), 4.96 (d, 1H, J=1.6 Hz), 5.06 (d, 1H, J =1.6 Hz), 7.16–7.52 (m, 10H, aromatic).

Example 6

7α-chloro-2-spiro (2',2'-diphenyl)cyclopropyl-3-methyl-3-cephem-4-phenylcarbonyl 1,1-dioxide Step A:

7α-Chloro-3-methyl-3-cephem-4-phenylcarbonyl 1,1-dioxide

A solution of 7α-chloro-3-methyl-3-cephem-4-carboxylic acid 1,1-dioxide (934 mg, 0.0035 mol) in dry methylene chloride (25 ml) was treated at ice-temperature with oxalyl chloride (592 mg) and two drops of DMF. The reaction mixture was stirred at ice-temperature for 15 min and at room temperature for 30 min; solvent was removed under reduced-pressure. The residue was dissolved in dry THF (25 ml) cooled to −70° C., anhydrous aluminium trichloride (327 mg, 0.00245 mol) was added and then phenyl magnesium bromide (4.5 ml, 1(M) THF solution). The reaction mixture was stirred for 5 min and poured into ice-water extracted with ethyl acetate, washed with brine, dried and concentrated (600 mg) which was purified over a silica gel column using hexane-ethyl acetate (3:2) as eluant to give the pure compound (103 mg) as a white solid. This product was directly used for the next step.

Step B:

7α-Chloro-2-exomethylene-3-methyl-3-cephem-4-phenylcarbonyl 1,1-dioxide

7α-Chloro-3-methyl-3-cephem-4-phenylcarbonyl 1,1-dioxide (103 mg, 0.000316 mol) was dissolved in a mixture of 1,4-dioxane (6 ml) and t-BuOH ml). To this mixture formaldehyde solution (37%, 0.1 ml and dimethylamine hydrochloride (77 mg, 0.000948 mol) were added and the mixture was heated to reflux at 90° C. for 2.5 h. The progress of the reaction was monitored by tlc. After the reaction was over the mixture was cooled to room temperature, diluted with 60 ml of methylene chloride, washed with water (4×10 ml), dried and concentrated to give a white solid (108 mg).

A portion of the above compound was crystallized from methylene chloride-ether, m.p. 245° C., decomp.

$^1H$ NMR (200 MHz, $CDCl_3$): δ1.85 (s, 3H), 5 34 (d, 1H, J=2.0 Hz), 5.49 (d, 1H, J=2.0 Hz), 6.17 (d, 1H, J=2.0 Hz), 6.66 (d, 1H, J=2.0 Hz), 7.51–7.97 (m, 5H, aromatic).

Step C: 7α-Chloro-2-spiro (2',2'-diphenyl)cyclopropyl-3-methyl-3-cephem-4-phenylcarbonyl 1,1-dioxide To a stirred solution of 7α-chloro-2-exomethylene-3-methyl-3-cephem-4-phenylcarbonyl 1,1-dioxide (70 mg, 0.000207 mol) in dry methylene chloride (10 ml) at room temperature was added diphenyldiazomethane (48 mg, 0.000249 mol) and the reaction mixture was stirred at room temperature for 1 h, solvent was removed under reduced pressure and the crude product (123 mg) was purified over a silica gel column using hexane-ethyl acetate (3:2) mixture, the product obtained (105 mg) was further purified by preparative tlc, 50 mg; mp 145°–147° C. (ethyl acetate-hexane).

IR (KBr) ) ν1793, 1664 $cm^{-1}$.

$^1H$ NMR (200 MHz, $CDCl_3$): δ0.77 (s, 3H, $CH_3$), 2.33 (d, 1H, J=7.0 Hz, cyclopropyl), 3.0 (d, 1H, J 7.0 Hz, cyclopropyl), 5.08 (d, 1H, J=2.0 Hz), 5.25 (d, 1H, J=2.0 Hz), 7.18–7.80 (m, 15H, aromatic).

Example 7

7α-Chloro-2-spiro(2',2'-diphenyl)cyclopropyl-3-methyl-3-cephem-4-t-butylcarbonyl 1,1-dioxide To a stirred solution of 7α-chloro-2-exomethylene-3-methyl-3-cephem-4-t-butylcarbonyl 1,1-dioxide (73 mg, 0.00023 mol, prepared according to Step B, Example 6) in dry methylene chloride (10 ml) at room temperature was added diphenyldiazomethane (54 mg, 0.000276 mol) and the reaction mixture was stirred at room temperature for a period of 3 hours. Solvent was removed under reduced pressure and the product (130 mg) was purified over a silica gel column using hexane-ethyl acetate mixture (8:2). The pure compound obtained (22 mg) was crystallized from ethyl acetate-hexane, m. p. 185°–187° C., decomp.

IR(KBr)ν1797, 1715, 1615 $cm^{-1}$.

$^1H$ NMR (200 MHz, $CDCl_3$): δ1.10 (s, 3H, $CH_3$), 1.56 (s, 9H, $Bu^t$), 2.37 (d, 1H, J=7.1 Hz, cyclopropyl), 2.96 (d, 1H, J=7.1 Hz, cyclopropyl), 5.0 (d, 1H, J=2.0 Hz), 5.20 (d, 1H, J=2.0 Hz), 7.23–7.49 (m, 10H, aromatic).

What is claimed is:

1. A 2-spirocyclopropyl 4-acylcephem sulfone of the formula (I)

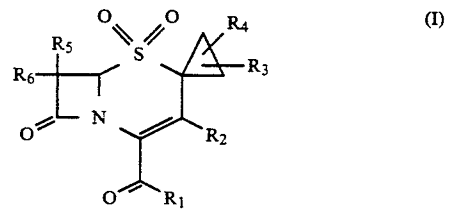

(I)

wherein $R_1$ is hydrogen; or $C_{1-12}$ straight or branched alkyl; or $C_{2-10}$ alkenyl; or $C_{2-10}$ alkynyl; or $C_{3-8}$ cycloalkyl; or $C_{6-10}$ aryl; or aralkyl; or aralkenyl; or aralkynyl; or (cycloalkyl)alkyl; or a monocyclic or polycyclic, saturated or unsaturated heterocyclic group containing from 1 to 4 of any one or more of the heteroatoms N, S, or O in each heterocyclic ring; or a fused polycyclic saturated or unsaturated heterocyclic group containing from 1 to 4 of any one or more of the heteroatoms N, S, or O in each heterocyclic ring; or heterocyclylalkenyl; or heterocyclylakynyl; wherein the heterocyclyl, alkyl, alkenyl, and alkynyl groups are as defined above; wherein each of the above organic radicals is unsubstituted or substituted by one or more atoms or groups selected from chloro, bromo, fluoro, cyano, azido, nitro, formyl, $C_{1-4}$ alkyl, trifluoromethyl, $C_{2-4}$ alkenyl, $C_{2-4}$ alkynyl, $C_{3-6}$ cycloalkyl, hydroxy, alkoxy, carboxy, $—(CH_2)_mCOOH$, $—(CH_2)_mCOR_{10}$, $—COR_{10}$, $—COCF_3$, $—CONH_2$, $—CONHR_{10}$, $—NH_2$, $—NH_{10}$, $—NR_{10}R_{11}$, $—NHSO_2R_{10}$, $—NHCOR_{10}$, $—NHC(=NH)NH_2$, $—OCOR_{10k}$, $—OC(O)NH_2$, $—SH$, $—SR_{10}$, $—S(O)R_{10}$, or $—SO_3H$ $R_2$ is selected from hydrogen; or chloro, bromo, or fluoro; or $C_{1-6}$ alkyl; or -trifluoromethyl; or $—C_{2-6}$ alkenyl; or $—C_{2-6}$ alkynyl; or $—C_{3-8}$ cycloalkyl, or $—OR_7$; or $—S(O)_nR_7$; or —CHO; or —COOH; or $—CH_2—O—R_7$; or $—CH_2S(O)_nR_7$; or $—C(O)R_7$; or $—C(O)OR_7$or $—CH_2OC(O)R_7$; or $—CH_2SC(O)R_7$; or $—CH_2Cl$; or $—CH_2$; or $—CH_2OC(O)NH_2$; or $—CH_2NR_7R_8$; or $—CH_2—NH(C_{1-4}$ alkyl); or $—CH_2—NH-C(O)R_7$; or $—CH_2—N^{\oplus}R_7R_8R_9$; or $—CH_2—S-(O)_nHet$; wherein the $—C_{2-6}$ alkenyl, $—C_{2-6}$ alkynyl, or the $C_{1-4}$ alkyl of the $CH_2—NH(C_{1-4}$ alkyl) may be unsubstituted or substituted by one or more atoms or groups selected from the chloro, bromo, fluoro, cyano, azido, nitro, formyl, $C_{1-4}$ alkyl, trifluoromethyl, $C_{2-4}$ alkenyl, $C_{2-4}$ alkynyl, $C_{3-6}$ cycloalkyl, hydroxy, alkoxy, carboxy, $—(CH_2)_mCOOH$, $—(CH_2)_mCOOR_{10}$, $—COR_{10}$, $—COCF_3$, $—CONH_2—CONHR_{10}$, $—NH_2$, $—NHR_{10}$, $—NR_{10}R_{11}$, $—NHSO_2R_{10}$, $—NHCOR_{10}$, $—NHC(=NH)NH_2$, $—OCOR_{10}$, $—OC(O)NH_2$, —SH, $—SR_{10}$, $—S(O)R_{10}$, or $—SO_2H$;

$R_3$ and $R_4$ are the same or different and may be hydrogen; or $C_{1-6}$ straight or branched alkyl group; or $C_{6-10}$ aryl group; or $C_{3-8}$ cycloalkyl group; or aralkyl group; or saturated or unsaturated monocyclic or fused polycyclic 3–8 membered heterocyclic group containing at least one heteroatom chosen from O, S, and N; or a halogenated $C_{1-6}$ alkyl; or a hydroxy $C_{1-6}$ alyl; or $—CH_2COOH$; or —COOH; or $—COOC_{1-6}$ alkyl group; or $—CH_2COOC_{1-6}$ alkyl;

$R_5$ is $R_1$; or $—O—R_1$; or $—S(O)_nR_1$; $—OC(O)R_1$; $—OSO_2R_1$; or $—NHC(O)R_1$; or —NH—Z; or halogen;

$R_6$ is hydrogen; or $C_{1-4}$ alkyl; or $C_{1-4}$ alkoxy; or halogen;

$R_7$, $R_8$ and $R_9$ are the same or different, and may be hydrogen; or $C_{1-6}$ lower straight or branched alkyl; or $C_{2-6}$ alkenyl; or $C_{2-6}$ alkynyl; or $C_{3-8}$ cycloalkyl; or $C_{6-10}$ aryl; or aralkyl; or saturated or unsaturated monocyclic or fused polycyclic 3 to 8 membered heterocyclic ring containing at lest one heteroatom chosen from O, S, and N; or, at least two of them, taken together with the nitrogen atom to which they are attached, form a heterocyclic ring;

$R_{10}$ and $R_{11}$ may be the same or different and represents $C_{1-6}$ straight or branched alkyl, phenyl, or benzyl;

Z is hydrogen; a mono-peptide composed of D or L -amino acids with the terminal amino group optionally acylated by $—C(O)R_1$ or $—C(O)OR_1$; or a di-peptide composed of D or L -amino acids with the terminal amino group optionally acylated by $—C(O)R_1$ or $—C(O)OR_1$; or a tripeptide composed of D or L -amino acids with the terminal amino group optionally acylated by $—C(O)R_1$ or $—C-(O)OR_1$;

Het is a saturated or unsaturated monocyclic or fused polycyclic 3 to 8 membered heterocyclic ring containing at least one heteroatom chosen from O, S and N;

m is 0, 1, 2 or 3; and n is 0, 1 or 2.

2. A compound according to claim 1 of the formula (I)

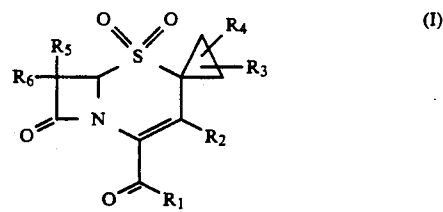

(I)

wherein $R_1$ is hydrogen; or methyl; or ethyl; or tert-butyl; or n-butyl; or phenyl; or benzyl; or dimethylphenyl; or diphenylmethyl, or propenyl;

$R_2$ is selected from hydrogen; or chloro; or methyl; or trifluoromethyl, chloromethyl; or bromomethyl; or hydroxymethyl; or acetoxymethyl; or acetylthiomethyl; or carbamoyloxymethyl; or hydroxy, methoxy, vinyl, cyclopropyl; or formyl; or carboxy, methoxycarbonyl; or ethoxycarbonyl; or methoxymethyl; or ethoxymethyl; or phenoxymethyl; or 3-pyridyloxymethyl; or methylthiomethyl; or phenylthiomethyl; or methylsulphonylmethyl; or phenylsulphonylmethyl; or aminomethyl; or $C_{1-4}$ alkylamino methyl wherein the alkyl is either unsubstituted or substituted by a carboxy group; or a quaternary ammonium group; or $CH_2—S(O)_nHet$;

$R_3$ and $R_4$ are the same or different and are hydrogen; or methyl; or ethyl; or phenyl; or cycloalkyl; or aralkyl; or saturated or unsaturated monocyclic or fused polycyclic 3–8 membered heterocyclic groups containing at least one heteroatom chosen from O, S, and N; or —COOH; or $—CH_2COOH$; or $—COOC_{1-6}$ alkyl; or $—CH_2COOC_{1-6}$ alkyl;

$R_5$ is selected from hydrogen; or chloro; or fluoro; or bromo; or $C_{1-4}$ alkyl; or methoxy; or ethoxy; or isopropoxy or phenoxy; or methylthio; or formyloxy; or acetoxy; or phenylacetoxy; or mesyloxy; or tosyloxy; or formamido; or acetamido; or trifluoroacetamido; or chloroacetamido; and $R_6$ is hydrogen; or chloro; or bromo; or fluoro; or $C_{1-4}$ alkyl; or $C_{1-4}$ alkoxy.

3. A compound according to claim 2, which is selected from the group consisting of:

7α-methoxy-2-spiro(2',2'-diphenyl)cyclopropyl-3-methyl-3-cephem-4-ethylcarbonyl 1,1-dioxide;

7α-methoxy-2-spiro (2',2'-diphenyl)cyclopropyl-3-methyl-3-cephem-4-butylcarbonyl 1,1-dioxide;

7α-methoxy-2-spiro (2',2'-diphenyl)cyclopropyl-3-methyl-3-cephem-4-methylcarbonyl 1,1-dioxide;

7α-methoxy-2-spiro (2',2'-diphenyl)cyclopropyl-3-methyl-3-cephem-4-phenylcarbonyl 1,1-dioxide;

7α-methoxy-2-spiro (2',2'-diphenyl)cyclopropyl-3-methyl-3-cephem-4-tert-butylcarbonyl 1,1-dioxide;

7α-methoxy-2-spiro (2',2'-diphenyl)cyclopropyl-3-methyl-3-cephem-4-phenylcarbonyl 1,1-dioxide; and 7α-methoxy-2-spiro (2',2'-diphenyl)cyclopropyl-3-methyl-3-cephem-4-tert-butylcarbonyl 1,1-dioxide.

4. The compound of claim 1, wherein $R_2$ is a carboxy-substituted $CH_2—NH(C_{1-4}alkyl)$ group.

5. The compound of claim 1, wherein $R_2$ is $—CH_2—(O)_nHet$, and a Het selected from

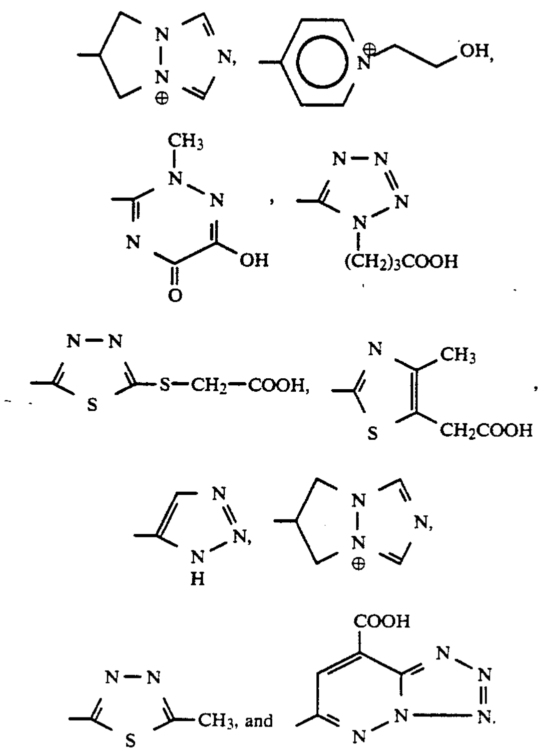

6. The compound of claim 2, wherein $R_2$ is a quaternary ammonium group selected from the group consisting of:

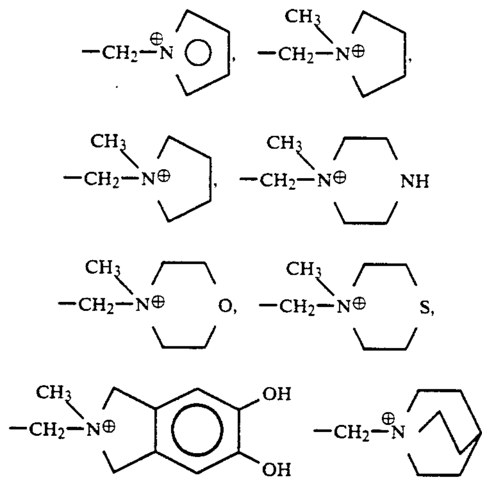

7. A pharmaceutical or veterinary composition comprising of an effective amount of a compound of claim 1 or a pharmaceutically or veterinarily acceptable salt thereof, in admixture with a pharmaceutically or veterinarily acceptable carrier.

8. A method of treatment for a mammal suffering from inflammatory or degenerative diseases and in need of such treatment, comprising administering an effective amount of the compound of claim 1 to said mammal.

9. The method of claim 8, wherein said disease is selected from the group consisting of emphysema, pulmonary emphysema, lupus, rheumatoid arthritis, osteoarthritis, cystic fibrosis, spondylitis, gout, psoriasis, chronic bronchitis, and acute respiratory distress syndrome.

10. The method of claim 8, wherein said compound is administered orally in a unit-dose amount ranging from 10 to 250 mg.

11. The method of claim 8, wherein said compound is administered parenterally in a unit-dose amount ranging from 0.02 to 10 mg/kg of body weight of said mammal.

12. The method of claim 8, wherein said compound is administered rectally.

13. A 2-spirocyclopropyl 4-acylcephem sulfone of the formula (I)

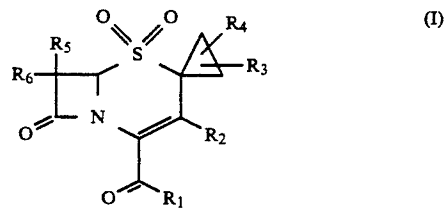

(I)

wherein $R_1$ is hydrogen; or $C_{1-12}$ straight or branched alkyl; or $C_{2-10}$ alkenyl; or $C_{2-10}$ alkynyl; or $C_{3-8}$ cycloalkyl; or $C_{5-8}$ cycloalkenyl; or $C_{6-10}$ aryl; or aralkyl; or aralkenyl; or aralkynyl; or (cycloalkyl)alkyl; or a monocyclic or polycyclic, saturated or unsaturated heterocyclic group containing from 1 to 4 of any one or more of the heteroatoms N, S, or O in each heterocyclic ring; or a fused polycyclic saturated or unsaturated heterocyclic group containing from 1 to 4 of any one or more of the heteroatoms N, S, or O in each heterocyclic ring; or heterocyclyalkenyl; or heterocyclylalkyny; wherein the heterocyclyl, alkyl, alkenyl, and alkynyl groups are as defined above; wherein each of the above organic radicals is unsubstituted or substituted by one or more atoms or groups selected from chloro, bromo, fluoro, cyano, azido, nitro, formyl, $C_{1-4}$ alkyl, trifluoromethyl, $C_{2-4}$ alkenyl, $C_{2-4}$ alkynyl, $C_{3-6}$ cycloalkyl, hydroxy, alkoxy, carboxy, $—(CH_2)_mCOOH$, $—(CH_2)_mCOOR_{10}$, $—COR_{10}$, $—COCF_3$, $—CONH_2$, $—CONHR_{10}$, $—NH_2$, $—NHR_{10}$, $—NR_{10}R_{11}$, $—NHSO_2R_{10}$, $—NHCOR_{10}$, $—NHC(=NH)NH_2$, $—OCOR_{10}$, $—OC(O)NH_2$, —SH, $—SR_{10}$, $—S(O)R_{10}$, or $—SO_3H$ $R_2$ is selected from hydrogen; or chloro, bromo, or fluoro; or $C_{1-6}$ alkyl; or -trifluoromethyl; or $—C_{2-6}$ alkenyl; or $—C_{2-6}$ alkynyl; or $—C_{3-8}$ cycloalkyl, or $—OR_7$; or $—S(O)_nR_7$; or —CHO; or —COOH; or $—CH_2—O—R_7$; or $—CH_2S(O)_nR_7$; or $—C(O)R_7$; or $—C(O)OR_7$; or $—CH_2OC(O)R_7$; or $—CH_2SC(O)R_7$; or $—CH_2Cl$; or $—CH_2Br$; or $—CH_2OC(O)NH_2$; or $—CH_2N^{\oplus}R_7R_8$; or $—CH_2—NH(C_{1-4}$ alkyl); or $—CH_2—NHC(O)R_7$; or $—CH_2—NR_7R_8R_9$; or $—CH_2—S(O)_nHet$;

$R_3$ and $R_4$ are the same or different and may be hydrogen; or $C_{1-6}$ straight or branched alkyl group; or $C_{6-10}$ aryl group; or $C_{3-8}$ cycloalkyl group; or aralkyl group; or saturated or unsaturated monocyclic or fused polycyclic 3–8 membered heterocyclic group containing at least one heteroatom chosen from O, S, and N; or a halogenated $C_{1-6}$ alkyl; or a hydroxy $C_{1-6}$ alkyl; or $—CH_2COOH$; or —COOH;

or $—COOC_{1-6}$ alkyl group; or $—CH_2COOC_{1-6}$ alkyl;

$R_5$ is $R_1$; or $—O—R_1$; or $—S(O)_nR_1$; $—OC(O)R_1$; $—OSO_2R_1$; or $—NHC(O)R_1$; or —NH—Z; or halogen;

$R_6$ is hydrogen; or $C_{1-4}$ alyl; or $C_{1-4}$ alkoxy; or halogen;

$R_7$, $R_8$ and $R_9$ are the same or different, and may be hydrogen; or $C_{1-6}$ lower straight or branched alkyl; or $C_{2-6}$ alkenyl; or $C_{2-6}$ alkynyl; or $C_{3-8}$ cycloalkyl; or $C_{6-10}$ aryl; or aralkyl; or saturated or unsaturated monocyclic or fused polycyclic 3 to 8 membered heterocyclic ring containing at least one heteroatom chosen from O, S, and N; or, at least two of them, taken together with the nitrogen atom to which they are attached, form a heterocyclic ring;

$R_{10}$ and $R_{11}$ may be the same or different and represents $C_{1-6}$ straight or branched alkyl, phenyl, or benzyl;

Z is hydrogen; a mono-peptide composed of D or L -amino acids with the terminal amino group optionally acylated by $—C(O)R_1$ or $—C(O)OR_1$; or a di-peptide composed of D or L -amino acids with the terminal amino group optionally acylated by $—C(O)R_1$ or $—C(O)OR_1$; or a tripeptide composed of D or L -amino acids with the terminal amino group optionally acylated by $—C(O)R_1$ or $—C(O)OR_1$;

Het is selected from

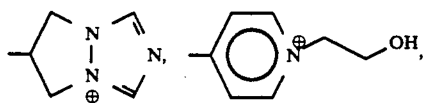

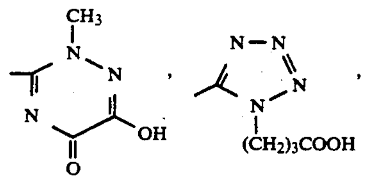

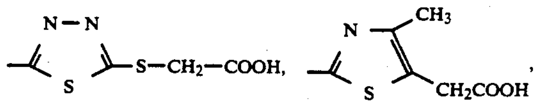

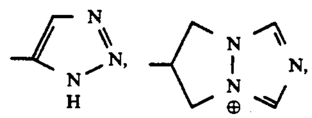

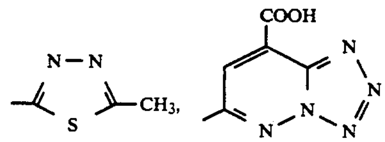

m is 0, 1, 2 or 3; and
n is 0, 1 or 2.

* * * * *